US008536319B2

(12) United States Patent
Schramm et al.

(10) Patent No.: US 8,536,319 B2
(45) Date of Patent: Sep. 17, 2013

(54) COMPOUNDS AND METHODS FOR DETECTING RICIN AND USES THEREOF

(75) Inventors: Vern L. Schramm, New Rochelle, NY (US); Setu Roday, Arlington, MA (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 722 days.

(21) Appl. No.: 12/308,447

(22) PCT Filed: Jun. 28, 2007

(86) PCT No.: PCT/US2007/015145
§ 371 (c)(1),
(2), (4) Date: Jul. 26, 2010

(87) PCT Pub. No.: WO2008/105796
PCT Pub. Date: Sep. 4, 2008

(65) Prior Publication Data
US 2011/0053146 A1  Mar. 3, 2011

Related U.S. Application Data

(60) Provisional application No. 60/817,624, filed on Jun. 29, 2006.

(51) Int. Cl.
| C07H 21/04 | (2006.01) |
| C07H 19/04 | (2006.01) |
| C12Q 1/68 | (2006.01) |
| C12P 19/34 | (2006.01) |
| B01L 3/00 | (2006.01) |

(52) U.S. Cl.
USPC ......... 536/24.1; 536/26.6; 435/6.1; 435/91.1; 435/91.2; 422/430

(58) Field of Classification Search
USPC .............. 536/24.3, 26.6; 435/6.1, 91.1, 91.2; 422/430
See application file for complete search history.

(56) References Cited

U.S. PATENT DOCUMENTS

| 6,864,056 | B1 | 3/2005 | Davies et al. |
| 7,019,129 | B1 | 3/2006 | Cook et al. |
| 7,777,025 | B2 | 8/2010 | Schramm et al. |
| 2004/0172684 | A1 | 9/2004 | Kovalic et al. |
| 2007/0269448 | A1 | 11/2007 | Schramm et al. |
| 2011/0136106 | A1 | 6/2011 | Schramm |
| 2011/0201674 | A1 | 8/2011 | Schramm et al. |

FOREIGN PATENT DOCUMENTS

WO   WO 2005/023203 A2   3/2005

OTHER PUBLICATIONS

"PCT Notification Concerning Transmittal of International Preliminary Report on Patentability" dated Jan. 22, 2009 issued by The International Bureau of WIPO in connection with PCT/US2007/015145. (8 pages).

Marras S A E et al., entitled Multiplex detection of single-nucleotide variations using molecular beacons, Genetic Analysis Biomolecular Engineering 14 (1999) 151-156.

Invitation to Pay Additional Fees and, Where Applicable, Protest Fee, dated Sep. 2008 from the International Searching Authority in connection with PCT Int'l Patent Application No. PCT/US2007/15145, 2 pages.

*Primary Examiner* — Jezia Riley
(74) *Attorney, Agent, or Firm* — Amster, Rothstein & Ebenstein LLP

(57) ABSTRACT

This application provides fluorescent probes, substrates, kits and methods for detecting the presence or absence of an enzyme, such as ricin, that catalyzes the release of adenine from a GAGA RNA tetraloop.

30 Claims, 16 Drawing Sheets

A)

B)

C

D

COMPOUNDS AND METHODS FOR DETECTING RICIN AND USES THEREOF

CROSS-REFERENCE TO RELATED APPLICATIONS

This application is a U.S. national stage entry under 35 U.S.C. §371 of PCT International Patent Application No. PCT/US2007/015145, filed Jun. 28, 2007, and claims priority to U.S. Provisional Patent Application No. 60/817,624, filed Jun. 29, 2006, the contents of which are incorporated herein by reference in their entirety.

STATEMENT OF GOVERNMENT SUPPORT

This invention was made with government support under grant number CA72444 awarded by the National Institutes of Health. The government has certain rights in the invention.

FIELD OF THE INVENTION

The present invention relates to compounds and methods for detecting ricin, which is both a bioterrorist agent and an agent used in immunochemotherapy. The invention also provides compounds and methods for detecting the presence of enzymes that catalyzes the release of adenine from a GAGA RNA tetraloop.

BACKGROUND OF THE INVENTION

Throughout this application various publications are referred to in parenthesis. Citations for these references may be found at the end of the specification immediately preceding the claims. The disclosures of these publications are hereby incorporated by reference in their entireties into the subject application to more fully describe the art to which the subject application pertains.

Ricin is a cytotoxic heterodimeric protein isolated from castor beans. Ricin inhibits protein synthesis in cells by cleavage of the N-glycosidic bond of a specific adenosine in a universally conserved GAGA hairpin motif of the 28S subunit of eukaryotic ribosomal RNA (rRNA). The catalytic activity of this heterodimeric protein resides in the ricin toxin A-chain (RTA) and inhibits elongation factor binding to the ribosome, leading to inhibition of protein synthesis and cell death (Endo et al. 1988). The ricin B-chain is a galactose specific lectin that binds to cell surface receptors, thus serving to direct the A-chain for internalization by receptor-mediated endocytosis.

Ricin has very high mammalian toxicity, in the μg/kg range. As such, it has been used in political assassination and has been developed to be used as a terrorist weapon (Hesselberth et al. 2000, Yan et al. 1997). Ricin is categorized as a class B bioterrorist agent. RTA has also been covalently bound to antibodies to be utilized in the design of "magic bullet" immunotoxins, with considerable anticancer activity (Baluna et al. 1999, Engert et al. 1998, O'Toole et al. 1998).

Detection of RTA is important given its potential lethality (Eiklid et al. 1980, Remnick 1992). Current probes for ricin employ ELISA (Shyu et al. 2002), array based immunoassays (Rubina et al. 2005), atomic force microscopy (Maliuchenko et al. 2004), mass spectrometry (Fredriksson et al. 2005) and molecular beacon aptamers (Kirby et al. 2004).

SUMMARY OF THE INVENTION

The present invention is directed to compounds and methods for detecting ricin through the catalytic activity of the ricin toxin A-chain (RTA).

The invention provides fluorescent probes for detecting the presence or absence of an enzyme such as ricin that catalyzes the release of adenine from a GAGA RNA tetraloop, where the fluorescent probes comprise a fluorophore, a quencher, and a nucleic acid that forms a hairpin loop, wherein the hairpin loop comprises TCXC, where C is cytidylate or deoxycytidylate, T is thymidylate, and X is T or a pyrene deoxynucleoside.

The invention also provides substrates for detecting the presence or absence of an enzyme such as ricin that catalyzes the release of adenine from a GAGA RNA tetraloop, where the substrates comprises a compound having a hairpin loop comprising 5'-GAGA-3' or 5'-G$_d$AGA-3', wherein A is adenylate, $_d$A is deoxyadenylate, and G is guanylate.

The invention further provides kits containing the fluorescent probes and substrates disclosed herein for detecting the presence or absence of an enzyme such as ricin.

In addition, the invention provides methods of detecting the presence or absence of an enzyme that catalyzes the release of adenine from a GAGA RNA tetraloop, where the methods comprise contacting one of the fluorescent probes disclosed herein with a substrate for the enzyme or with a reaction product created by catalysis of the substrate by the enzyme, under conditions appropriate for the enzyme to catalyze the substrate, wherein a change in intensity of the fluorescent probe indicates that the substrate has been cleaved by the enzyme and that the enzyme is present and an absence of change in intensity in the fluorescent probe is indicative of the absence of the enzyme.

BRIEF DESCRIPTION OF THE FIGURES

FIG. 1. Overview of DNA beacon design. There is a differential fluorescence resonance energy transfer (FRET) response when the hairpin molecular beacon MB is annealed with either a perfectly complementary sequence (A-14) or one with a single base mismatch (ab-14). The two sequences are representative of the substrate and product of the reaction catalyzed by RTA. An unstable match is presented to the abasic site with the thymidine probe MB1. The beacon MB2 incorporates a pyrene deoxynucleoside and presents a stable match.

FIG. 2A-2B. Structures of molecular beacon MB1 and MB2. A) MB1 has a d(TCTC) hairpin loop and is labeled with fluorescein and black hole quencher-1 (BHQ-1) at its 5' and 3' ends respectively. B) MB2 has a pyrene deoxynucleoside in the tetraloop d(TCPyC) for specific pairing to an abasic site upon hybridization. MB2 is labeled with fluorescein at the 5' and a dabcyl group at the 3' end.

FIG. 3. The ESI spectrum confirming the mass of oligonucleotide MB1.

FIG. 4. Structure of 5'-dimethoxytrityl protected pyrene 2'-deoxyribose phosphoramidite for incorporation into MB2.

FIG. 5. HPLC trace of NAP-10 wash layer with the largest peak at 30 min confirmed by MALDI-TOF as MB2. The flow rate was 3.5 ml/min with the gradient shown in Table 1.

FIG. 6. HPLC of final purified MB2. The flow rate was 2.5 ml/min with the gradient in Table 1.

FIG. 7. MALDI spectrum of MB2. Calculated Mass: 5321.33, Observed Mass: 5320.97.

FIG. 8A-8B. Melting transitions for two of the heteroduplexes in this study, A) dab-14:MB2 and B) A-14:MB1.

FIG. 9A-9B. Detection of RTA in homogeneous solution.

RTA substrates (2 μM) were incubated with 125 nM enzyme at 37° C. for 30 min following which they were annealed with equimolar concentration of beacon probes. Measurements were at the excitation wavelength of fluorescein. Response of the dT probe MB1 (A) and the pyrene probe MB2 (B) to A-14-2dA before and after incubation with RTA ('A14-2dA': substrate and 'Prd': product of the RTA reaction.).

Figures 9A, 9B:
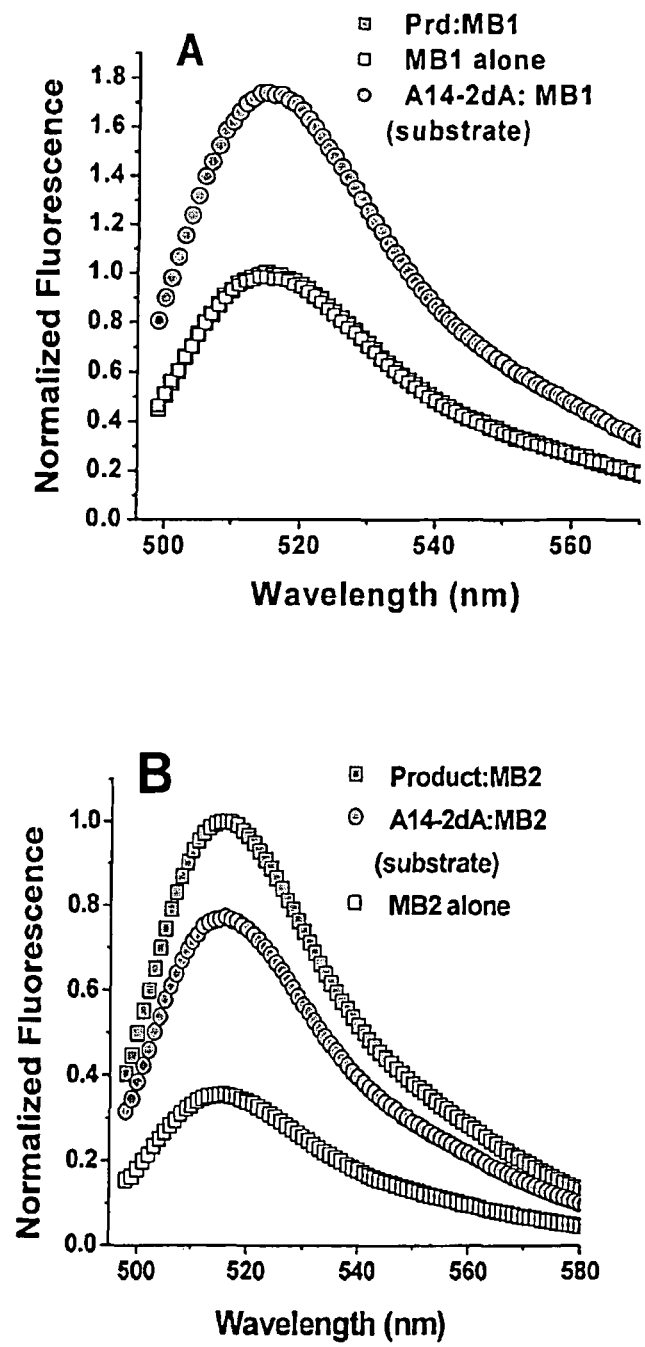
Figures 10A, 10B:
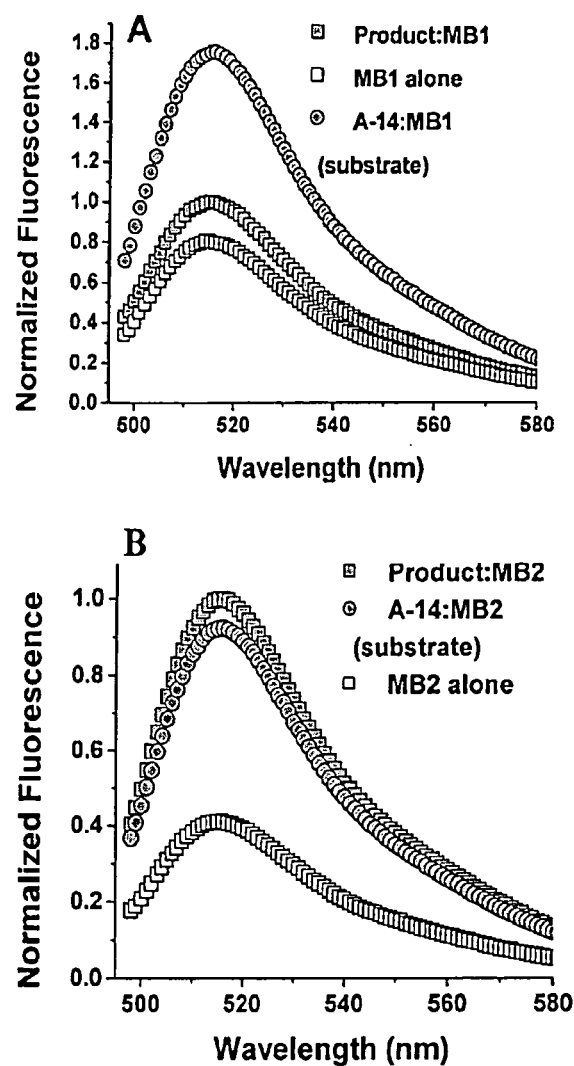

FIG. 10A-10B. Detection of RTA in homogeneous solution. Same as FIG. 9A-9B but using A14 instead of A14-2dA as the substrate of the RTA reaction.

FIG. 11A-11D. A, B: Hybridization of model sequences A-14 and dab-14 with MB1 (A) and MB2 (B) in 20 mM triethanolamine buffer containing 5 mM MgCl$_2$ and 50 mM KCl. C, D: Hybridization of A-14-2dA and dab-14 with MB1 (C) and MB2 (D) under the same conditions.

Figure 12:
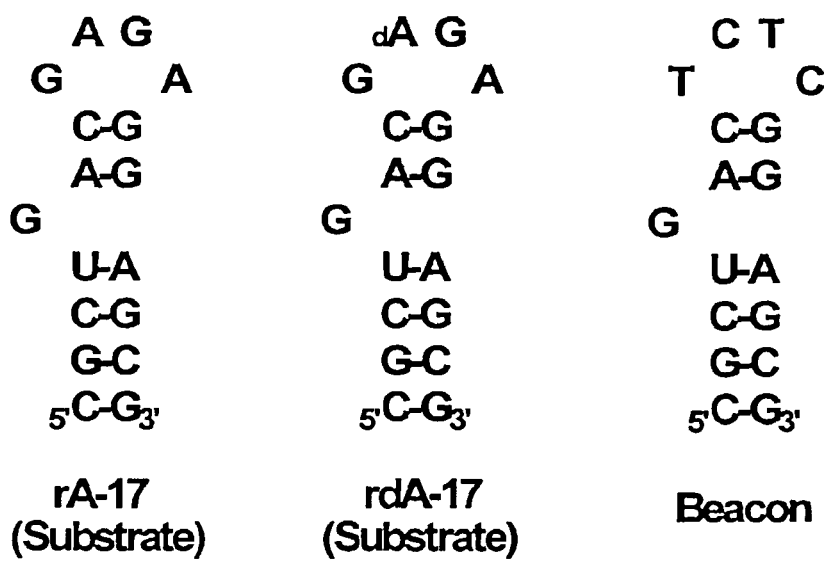

FIG. 12. Additional substrates and beacons for ricin detection. Examples are shown of the structures of additional substrates and of an additional beacon. The TCTC hairpin loop in the illustrated beacon can be replaced with a hairpin loop that incorporates a pyrene nucleoside in an analogous fashion to MB2.

Figure 13:
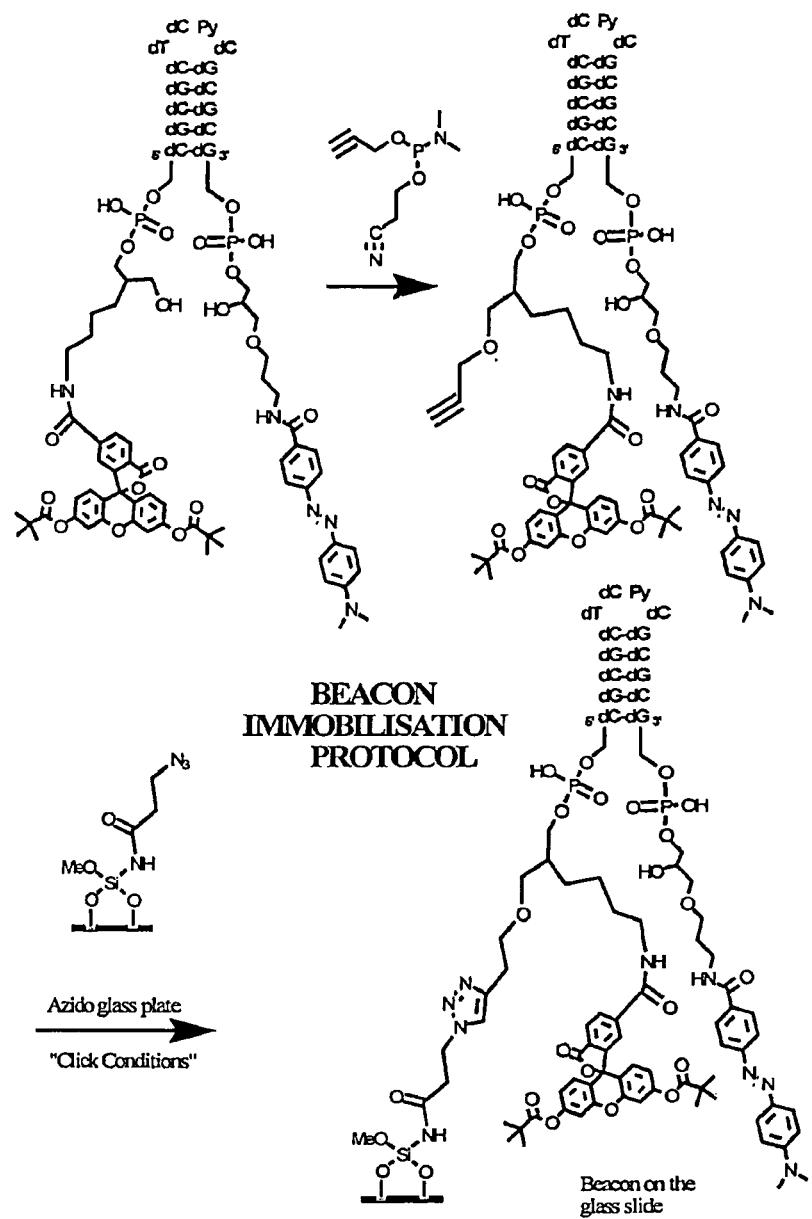

FIG. 13. Proposed scheme for immobilization of molecular beacons onto glass using click chemistry.

Figure 14:
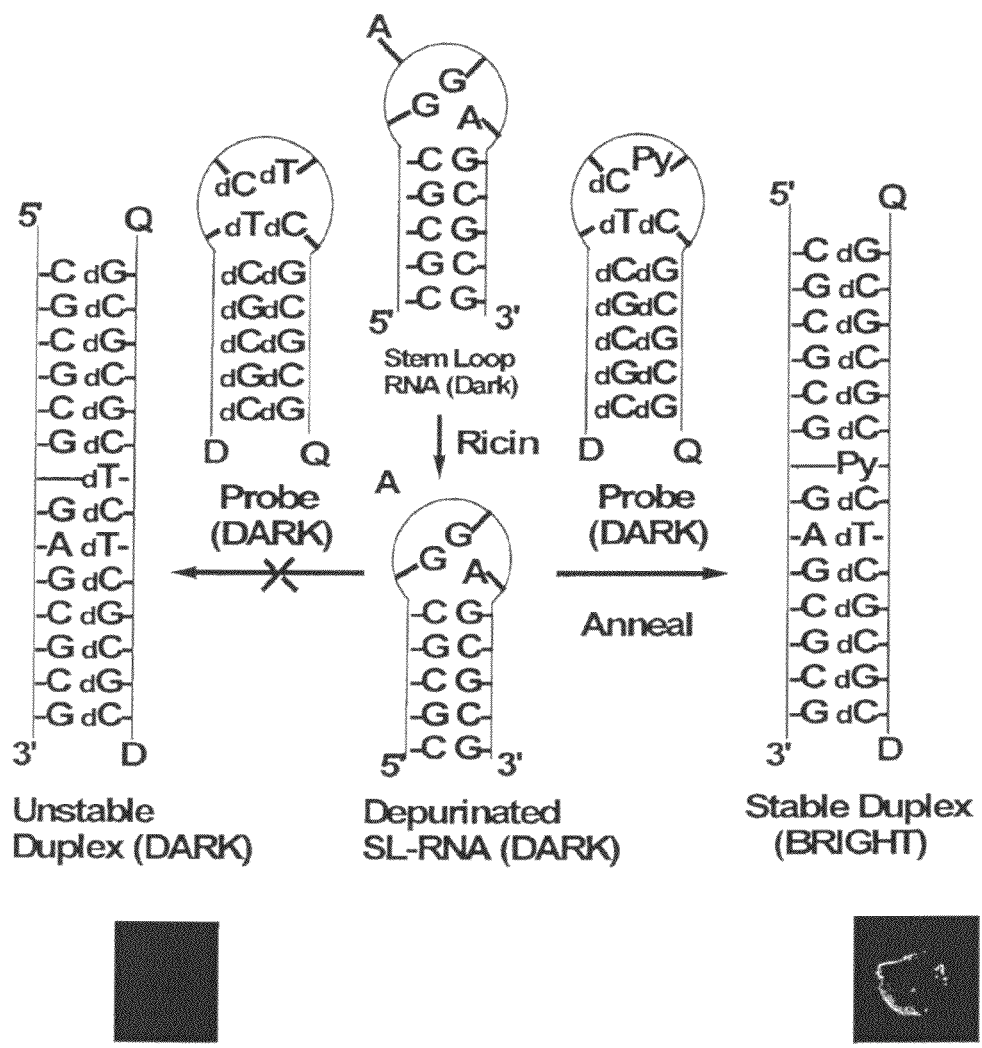

FIG. 14. Schematic of example of ricin detection. Ricin Toxin A-chain (RTA) hydrolyzes the N-glycosidic bond of a specific adenosine in the GAGA tetraloop of a 14-mer stem-loop RNA (center column of Figure). Also illustrated are two DNA beacons that can detect abasic site formation and thus RTA activity. Fluorescence resonance energy transfer (FRET) between a fluorophore/quencher pair in the 14-mer stem-tetraloop DNA beacons is disrupted only when the beacons are hybridized with RNA sequences that provide a perfect match. One beacon hybridizes selectively with the RTA substrate (far left of Figure). The second beacon incorporates a pyrene deoxynucleoside for specific recognition of the abasic site and hybridizes efficiently with the product of the RTA reaction (far right of Figure).

DETAILED DESCRIPTION OF THE INVENTION

The present invention provides a fluorescent probe for detecting the presence or absence of an enzyme that catalyzes the release of adenine from a GAGA RNA tetraloop, the fluorescent probe comprising: a fluorophore, a quencher, and a nucleic acid that forms a hairpin loop, wherein the hairpin loop comprises TCXC, where C is cytidylate or deoxycytidylate, T is thymidylate, and X is T or a pyrene deoxynucleoside. GAGA is the RNA sequence Guanylate-Adenylate-Guanylate-Adenylate. A preferred enzyme is ricin.

The fluorescent marker probe is based on fluorescence resonance energy transfer (FRET) between a fluorophore/quencher pair. The probe comprises molecular beacons (MBs), which are dual-labeled probes that have self-complementary ends that form a stem-loop structure (hairpin) in their native state. The hairpin forces the fluorophore reporter and quencher to be in close proximity to each other. Upon hybridization to a target, the reporter and quencher are separated and the molecular beacon becomes under goes a change in fluorescent intensity.

Various fluorophore-quencher pairs can be used. Preferred fluorophores include fluorescein, such as 6-carboxyfluorescein, rhodamine, cyanine, and TAMRA. Preferred quenchers include Black Hole Quencher Dye 1, Black Hole Quencher Dye 2, and a dabcyl group.

Preferably, the fluorescent probe contains between 9 and 21 nucleotides, for example 9-10, 13-14 or 16-17 nucleotides. The nucleic acid in the fluorescent probe can be deoxyribonucleic acid (DNA), ribonucleic acid (RNA), or DNA and RNA, or a Locked Nucleic Acid (LNA).

In a preferred example, the fluorescent probe has the formula:

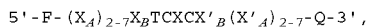

wherein $X_A$ and $X'_A$ are nucleotides selected from A (adenylate or deoxyadenylate), C (cytidylate or deoxycytidylate), G (guanylate or deoxyguanylate), T (thymidylate) and U (uridylate); wherein $(X_A)_{2-7}$ and $(X'_A)_{2-7}$ are 2 to 7 nucleotides in length; wherein $(X_A)_{2-7}$ is the same number of nucleotides as $(X'_A)_{2-7}$; and wherein each nucleotide in $(X_A)_{2-7}$ is a complementary base pair with the nucleotide in the corresponding location in $(X'_A)_{2-7}$; wherein one of $X_B$ and $X'_B$ is C and the other is G; wherein F is a fluorescein, a rhodamine, a cyanine, or TAMRA; wherein Q is Black Hole Quencher Dye 1, Black Hole Quencher Dye 2, or a dabcyl group; and wherein X is T or a pyrene deoxynucleoside.

As used herein, complementary base pairs form hydrogen bonds between the members of the pair and include the pairs A-T, T-A, C-G, G-C, A-U, U-A, G-U, U-G, A-G and G-A. Preferred complementary base pairs are C-G and G-C.

More specific examples of probes include probes having the formulas:

5'-F-$X_A X_A X_A X_A X_B$TCXCX'$_B$X'$_A$X'$_A$X'$_A$X'$_A$-Q-3', wherein F, $X_A$, $X_B$, G, T, X, and Q are as defined herein above;

5'-F-CGCGCTCXCGCGCG-Q-3', wherein C is deoxycytidylate, G is deoxyguanylate, and F, T, X, and Q are as defined herein above;

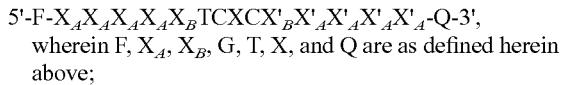

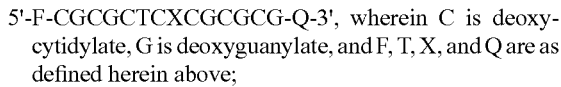

wherein Py is a pyrene deoxynucleoside;

5'-F-$X_A X_A X_B$TCXCX'$_B$X'$_A$X'$_A$-Q-3', wherein F, $X_A$, $X_B$, G, T, X, and Q are as defined herein above;

5'-F-CGCTCXCGCG-Q-3', wherein C is deoxycytidylate and G is deoxyguanylate;

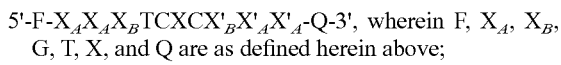

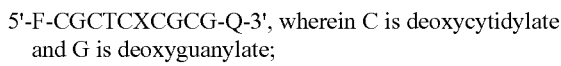

wherein Py is a pyrene deoxynucleoside.

A preferred fluorescent probe has the structure:

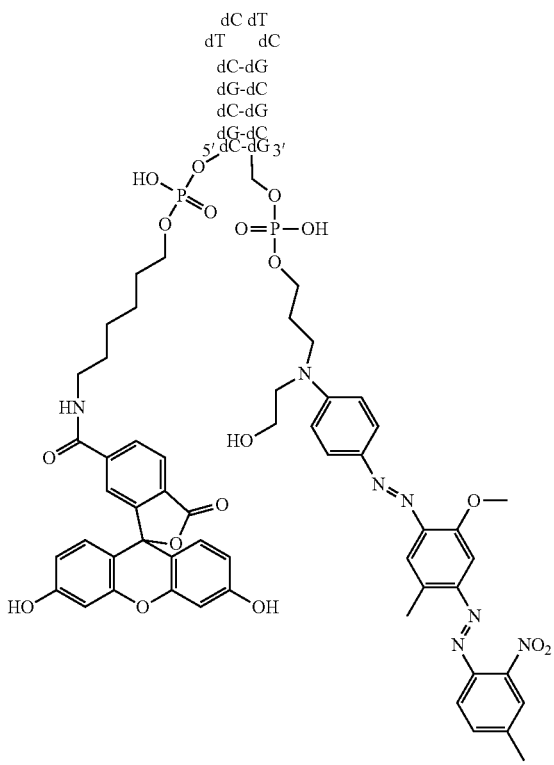

wherein dC is deoxycytidylate, dG is deoxyguanylate, and dT is thymidylate.

Another preferred fluorescent probe has the structure:

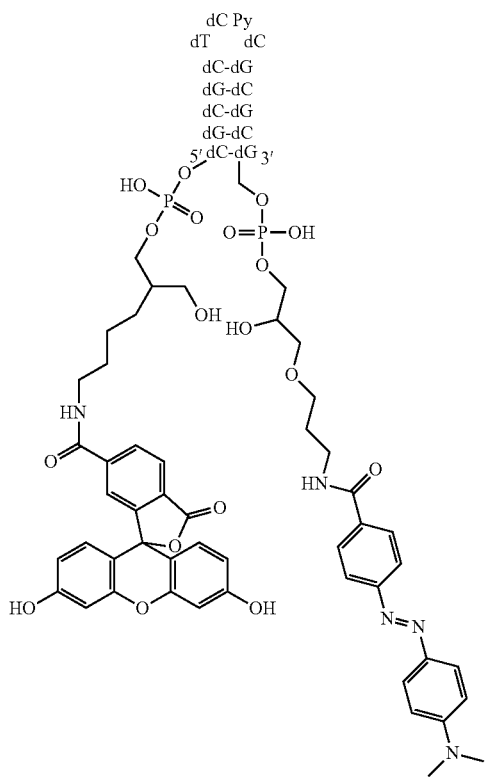

where Py is

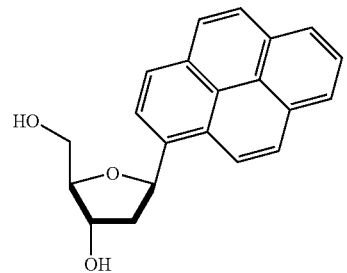

and
wherein dC is deoxycytidylate, dG is deoxyguanylate, and dT is thymidylate.

In another preferred example, the fluorescent probe has the formula:

5'-F-$(X_A)_{1-6}GX_AX_B$TCXCX'$_B$X'$_A$(X'$_A$)$_{1-6}$-Q-3', wherein G is guanylate or deoxyguanylate; wherein $X_A$ and X'$_A$ are nucleotides selected from A (adenylate or deoxyadenylate), C (cytidylate or deoxycytidylate), G (guanylate or deoxyguanylate), T (thymidylate) and U (uridylate); wherein $(X_A)_{1-6}$ and $(X'_A)_{1-6}$ are 1 to 6 nucleotides in length; wherein $(X_A)_{1-6}$ is the same number of nucleotides as $(X'_A)_{1-6}$; and wherein each nucleotide in $(X_A)_{1-6}$ is a complementary base pair with the nucleotide in the corresponding location in $(X'_A)_{1-6}$; wherein one of $X_B$ and X'$_B$ is C and the other is G; wherein F is a fluorescein, a rhodamine, a cyanine, or TAMRA; wherein Q is Black Hole Quencher Dye 1, Black Hole Quencher Dye 2, or a dabcyl group; and wherein X is T or a pyrene deoxynucleoside.

More specific examples include probes having the formulas:

5'-F-$X_AX_AX_AX_A$G$X_AX_B$TCXCX'$_B$X'$_A$X'$_A$X'$_A$X'$_A$X'$_A$X'$_A$-Q-3', wherein F, $X_A$, $X_B$, G, T, X, and Q are as defined herein above;

5'-F-CGCUGACTCXCGGAGCG-Q-3';

5'-F-CGCUGACTCTCGGAGCG(SEQ ID NO: 3)-Q-3'; and

5'-F-CGCUGACTCPyCGGAGCG-Q-3', wherein Py is a pyrene deoxynucleoside.

Different fluorescent probes can bind to a substrate for the enzyme or to a reaction product created by catalysis of a substrate by the enzyme. Similarly, depending on the fluorescent probe, the presence of the enzyme can be indicated by a decrease in fluorescent intensity or by an increase in fluorescent intensity. Probes where variable "X" in the sequence TCXC is thymidylate bind to a substrate for the enzyme and exhibit a decrease in fluorescent intensity when the enzyme cleaves the substrate. Probes where variable "X" is a pyrene deoxynucleoside bind to a reaction product created by catalysis of the substrate by the enzyme and exhibit an increase in fluorescent intensity when the enzyme cleaves the substrate and the probe binds to the reaction product.

The invention also provides a substrate for detecting the presence or absence of an enzyme that catalyzes the release of adenine from a GAGA RNA tetraloop, where the substrate comprises a compound having a hairpin loop comprising 5'-GAGA-3' or 5'-G$_d$AGA-3', wherein A is adenylate, $_d$A is deoxyadenylate, and G is guanylate. Examples of the substrate include compounds comprising: 5'-CGCGC- GAGAGCGCG-3' (SEQ ID NO:4), 5'-CGCGCG$_d$A-GAGCGCG-3' (SEQ ID NO:4), 5'-CGCUGACGAGAGGAGCG-3 (SEQ ID NO:5), 5'-CGCUGACG$_d$AGAGGAGCG-3 (SEQ ID NO:5), 5'-CGCGAGAGCG-3 (SEQ ID NO:6), or 5'-CGCG$_d$A-GAGCG-3 (SEQ ID NO:6), where C is cytidylate and U is uridylate. Preferably, the substrate comprises 10-21 nucleotides. The substrate can be, for example, a substrate for ricin, saporin, trichosanthin, gelonin or cinnamonin. Preferred substrates are substrates for ricin.

The invention further provides kits for detecting the presence or absence of an enzyme that catalyzes the release of adenine from a GAGA RNA tetraloop, wherein the kits comprise any one or more of the fluorescent probes disclosed herein. The fluorescent probe can be immobilized on a surface, for example a glass surface such as a glass slide. The kits can also include one or more substrates for the enzyme, such as any one or more of the substrates disclosed herein. The kits can also contain solutions for carrying out the detection procedure. Preferably, the kits contain an acidic buffer solution for incubating the sample to be tested for the presence or absence of the enzyme with a substrate for the enzyme. A preferred acidic buffer is potassium citrate buffer, preferably at pH 4.0. Preferably, the potassium citrate buffer contains ethylenediaminetetraacetic acid (EDTA). Another preferred acidic buffer is 10 mM sodium actetate, pH 4.0. Preferably, the kits contain a basic buffer solution for raising the pH of the acidic reaction mixture above pH 7.0 before the sample is incubated with the fluorescent probe. A preferred basic buffer is triethanolamine buffer, for example at pH 7.6. Other preferred basic buffers are Tris/HCl, pH 8.0, and sodium phosphate, pH 7.8. The kits can also include a device for measuring the pH of a solution, for example a pH test strip. The kits can be used for the detection of the presence or absence of enzymes, such as ricin, or for example saporin, trichosanthin, gelonin and cinnamonin. Preferred kits can be used for the detection of the presence or absence of ricin.

The invention further provides methods of detecting the presence or absence of an enzyme that catalyzes the release of adenine from a GAGA RNA tetraloop, where the method comprises contacting a fluorescent probe with a substrate for the enzyme or with a reaction product created by catalysis of the substrate by the enzyme, under conditions appropriate for the enzyme to catalyze the substrate, wherein a change in intensity of the fluorescent probe indicates that the substrate has been cleaved by the enzyme and that the enzyme is present and an absence of change in intensity in the fluorescent probe indicates the absence of the enzyme, wherein the fluorescent probe is any of the fluorescent probes disclosed herein. The method can further comprise contacting a first fluorescent probe with a substrate for the enzyme and contacting a second fluorescent probe with a reaction product created by catalysis of the substrate by the enzyme.

The method can further comprise providing a substrate for the enzyme, for example any of the substrates disclosed herein. Additional substrates for RTA that resembles the natural Sarcin-Ricin loop (SRL) of ribosomal RNA can also be used.

The method can further comprise incubating a sample to be tested for the presence or absence of the enzyme with a substrate for the enzyme under acidic conditions, for example pH 4.0, and then incubating the sample with the fluorescent probe under conditions above pH 7.0, for example pH 7.6.

The method can further comprise immobilizing the fluorescent probe on a surface, for example a glass surface such as a glass slide. The fluorescent probe can be immobilized on the glass using click chemistry. Click chemistry has been described, for example, in Seo et al. (2005).

The current work describes two types of probes. Probes of the type MB1 provide a negative control wherein only the substrate of the RTA reaction fluoresces brightly when annealed with MB1. Thus, the presence of the enzyme is detected when the enzyme catalyzes the substrate, and the MB1 fluorescent probe is dark. The fluorescence of the MB1 probe indicates that the substrate has not been catalyzed and is indicative of the absence of the enzyme. In contrast, with probe MB2, both substrate and product show an enhancement in fluorescence intensity. The product shows a (20-25%) increase in intensity over that of the substrate. The presence or absence of ricin can be determined unambiguously by using both types of probes simultaneously. In the case of MB1, only the substrate fluoresces whereas with MB2, both substrate and product can fluoresce brightly.

The methods described herein can be used to detect the release of adenine from a GAGA tetraloop, due for example to catalysis by the ricin-A chain or by another enzyme. The present invention can be used for the detection of ricin activity in suspect samples. If preferred, ricin can be cleaved to release the A-chain by cleaving the ricin disulfide bond. Similarly, the present invention can also be used for detection of ricin activity in patients treated with ricin immunochemotherapy, for example, in a blood sample from such patients. The present invention may be useful for the detection of other enzymes, including for example saporin, trichosanthin, gelonin and cinnamonin.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Overview

Figure 1:
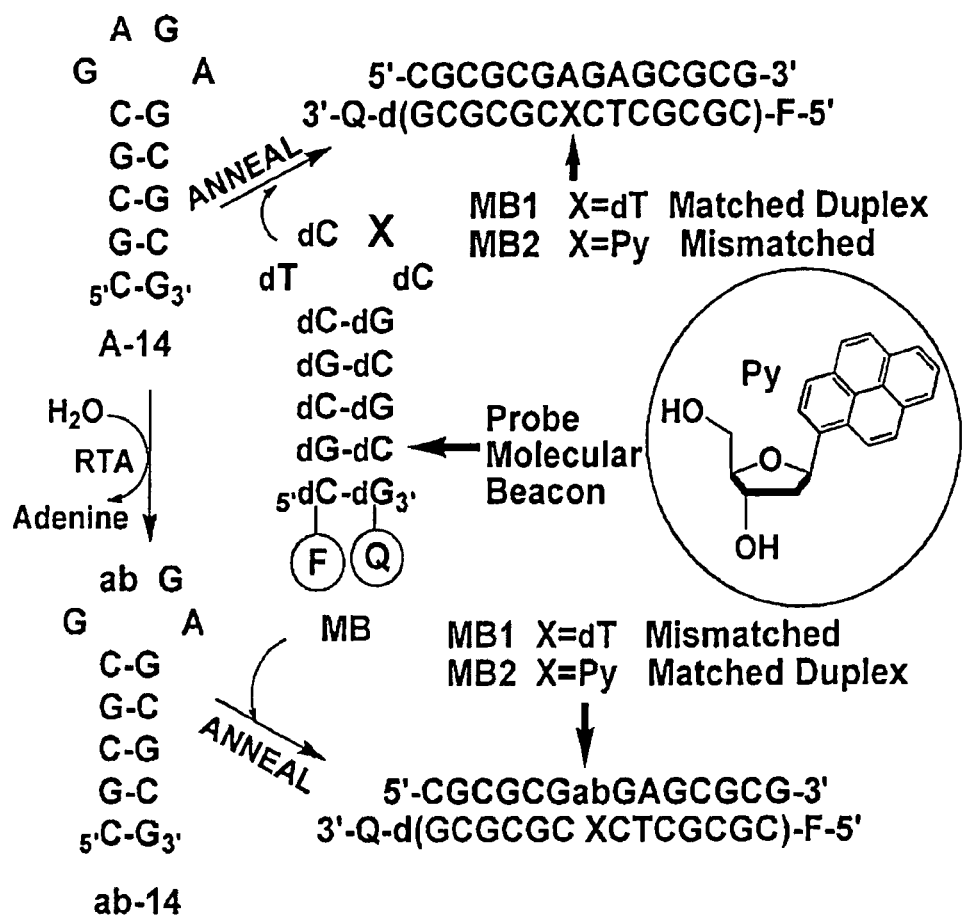

The present invention discloses a ricin probe design that is linked to the hydrolytic activity of RTA. RTA is know to catalyze site specific deadenylation of synthetic stem-loop RNA and DNA molecules containing a GAGA tetraloop motif at pH 4.0 (Chen et al. 1998). The $k_{cat}$ for the depurination of an all RNA stem-tetraloop substrate, A-14, at this site was determined to be 219±14 min$^{-1}$ and the $K_m$ for its binding was 8.1±0.7 µM (FIG. 1). The product of the RTA reaction, ab-14, bears an abasic site in the tetraloop. The inventors reasoned that differentiation between the presence of A-14 and ab-14 in a reaction mixture could be made possible by hybridization with a short 14-mer stem-tetraloop oligonucleotide sequence carrying a fluorophore and a quencher at its ends. In one case, A-14 would be completely complementary to the beacon sequence while in the other, ab-14 would be discriminated on the basis of a single base mismatch with that sequence.

Materials and General Experimental

RTA was purchased from Sigma. RNase inhibitors were purchased from Ambion (Austin, Tex.). Nucleoside phosphoramidites and other reagents for oligoribonucleotide synthesis were purchased from Glen Research (Sterling, Va.), and ChemGene Corp. (Ashland, Mass.). All other chemicals were purchased from Aldrich Chemical Co. (Milwaukee, Wis.) and were of the highest purity available. These reagents were used without further purification. Purification of reaction intermediates of the phosphoramidite synthetic pathway was completed by flash column chromatography using Merck silica gel 60 (230-400 mesh). Purification by HPLC was performed on a Waters 626 pump with a 996 photodiode array detector and using the Millennium software package. RNA concentrations were determined by UV-Vis measurements using a Cary 100 diode array spectrophotometer from Varian. Model RNA oligonucleotides A-14, A14-2dA and dab-14 were purchased from Dharmacon (Lafayette, Colo.).

Molecular Beacon MB1

Figure 2A:
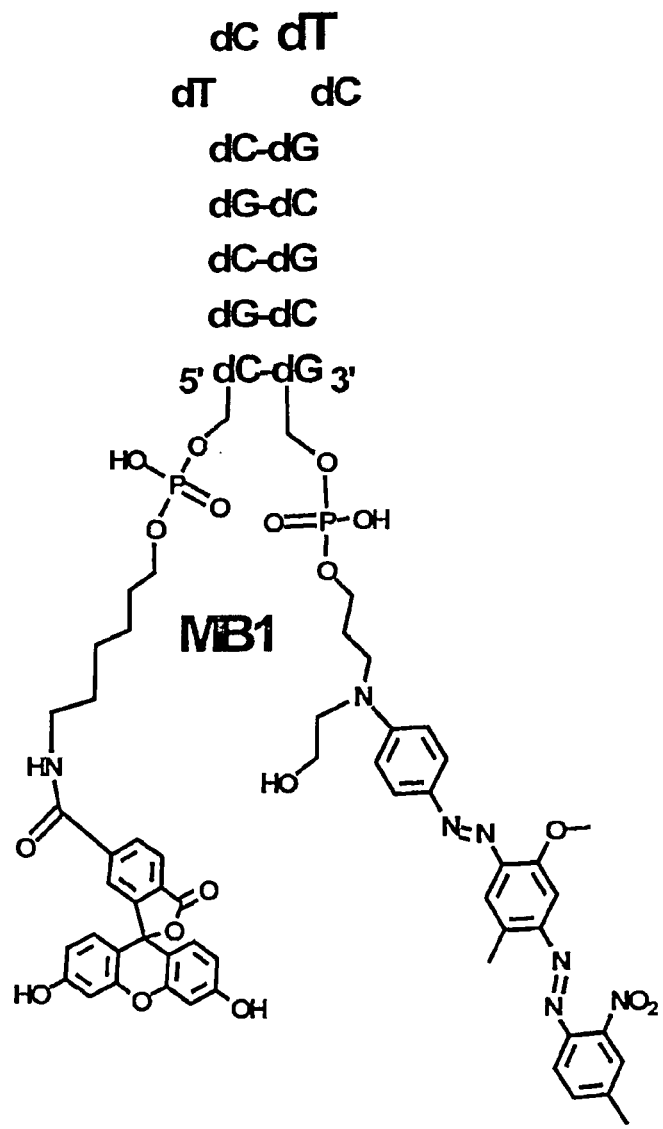
Figure 3:
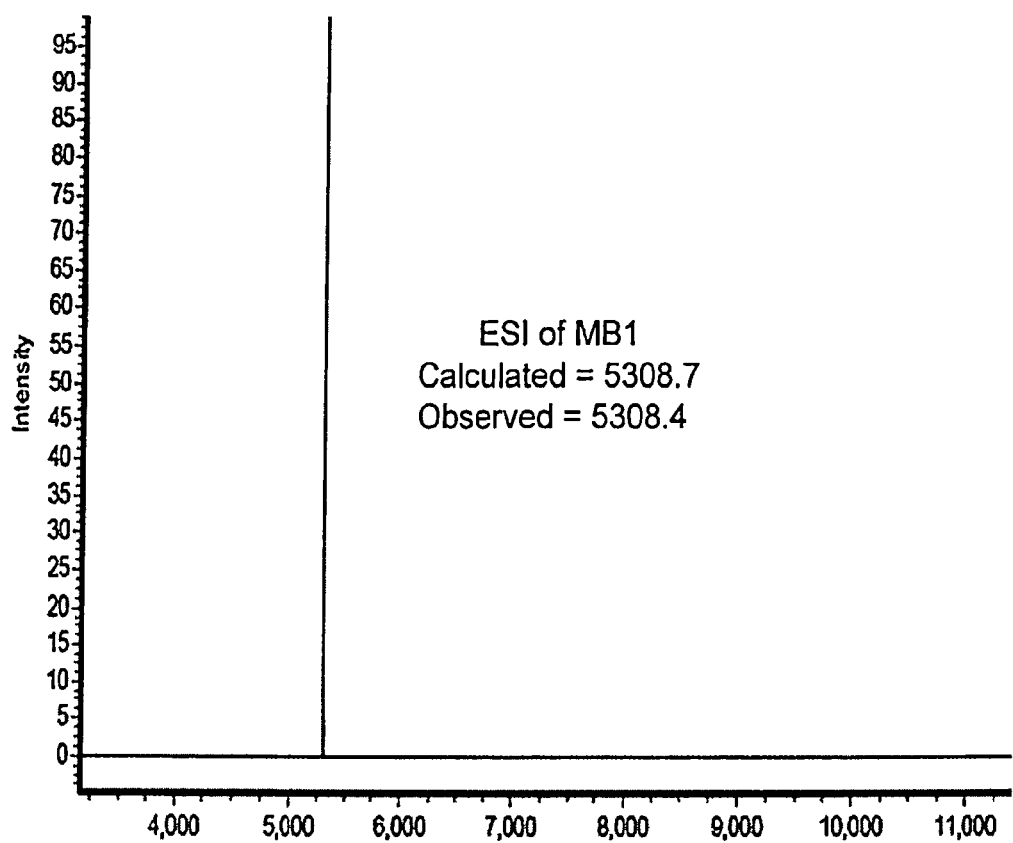

MB1 with the -TCTC- tetraloop sequence was designed based on kinetic information established for RTA hydrolysis of a 14-mer RNA sequence, A-14, with a -GAGA- tetraloop. The design was driven by the fact that TCTC in the 3'→45' direction is complementary to the RTA substrate's GAGA tetraloop. Integrated DNA Technologies was requested to synthesize the sequence with fluorescein at the 5'-end and BHQ-1 at the 3'-end. The structure of MB1 is shown in FIG. 2A. The ESI spectrum confirming the mass of this oligonucleotide is shown in FIG. 3.

Synthesis of the β-Pyrene Deoxynuceloside Phosphoramidite.

Figure 4:
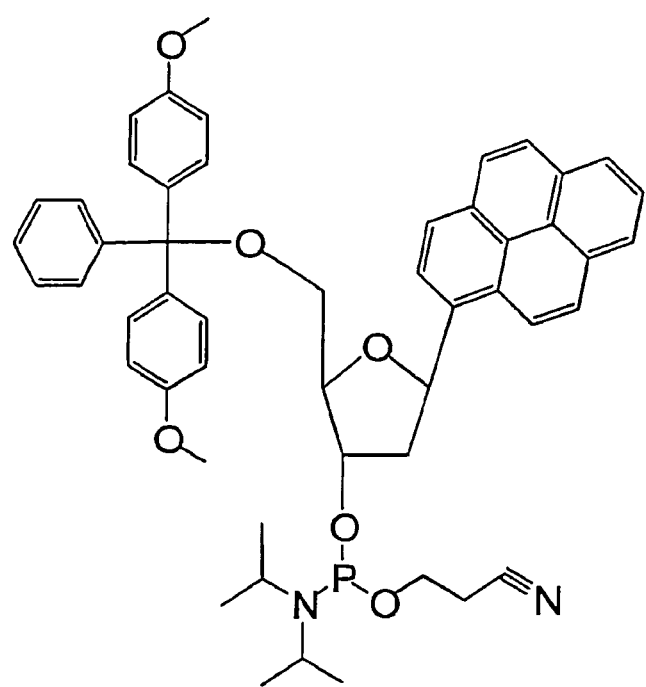

The synthesis of the pyrene phosphoramidite (FIG. 4) was reported by Ren et al. (1996). The modified method of Jiang et al. (2002) was used for its synthesis. The characterization of the intermediates in the synthetic pathway was according to published procedures and matched the reported data. The pyrene phosphoramidite, however, was used for oligonucleotide synthesis without further purification. No reduction in yields was observed on the synthesizer based on the monitoring of trityl data.

Synthesis and Purification of MB2.

Oligonucleotide MB2 was synthesized on a 1 μM scale in the DMT-off mode using an Expedite 8909 DNA/RNA synthesizer and following standard β-cyanoethyl phosphoramidite chemistry for DNA. 3'-Dabcyl CPG solid support and 5'-6-fluorescein phosphoramidite were used according to the manufacturer's recommendations. The crude β-pyrene deoxyribose phosphoramidite was introduced without further purification. A 15 min coupling time was used for the modified nucleoside. Cleavage of the oligonucleotide from the solid support and of the protecting groups on the bases was accomplished in one step with concentrated $NH_4OH$ at 25° C. for 12-14 hrs. The reaction mixture was then centrifuged to remove the solid support beads and the supernatant was evaporated to dryness under vacuum. All operations were carried out in the dark to avoid photobleaching of the fluorophores. The dry reaction pellet was then dissolved in 1 ml of sterile water and passed through a NAP-10 column. Both wash and elution layers were collected and evaporated to dryness under vacuum. The samples were then dissolved in sterile RNAase/DNAase free water and injected onto a reversed-phase C18 Waters Delta-Pak semi-prep column (7.8 mm×300 mm) and separated in 20 mM $NH_4OAc$ buffer, pH 6.6, containing 5% $CH_3CN$ under gradient conditions outlined in Table 1. A major putative MB2 peak was isolated from the NAP-10 wash layer with a gradient elution at 3.5 ml/min (FIG. 5), and its identity was confirmed by MALDI-TOF mass spectrometry. Additional purification of this peak gave a single symmetrical peak using the gradient in Table 1 with a slower flow rate of 2.5 ml/min (FIG. 6). Pure MB2 was then desalted on a Waters reverse phase C18 Sep-Pak cartridge. The oligonucleotide was then suspended in sterile water and its concentration determined by UV at 260 nm ($\epsilon$=182.1). A correction for the absorbance of pyrene was made based on the ratio of the pyrene absorbance at its $\lambda_{max}$ of 348 nm to that at 260 nm.

Figure 7:
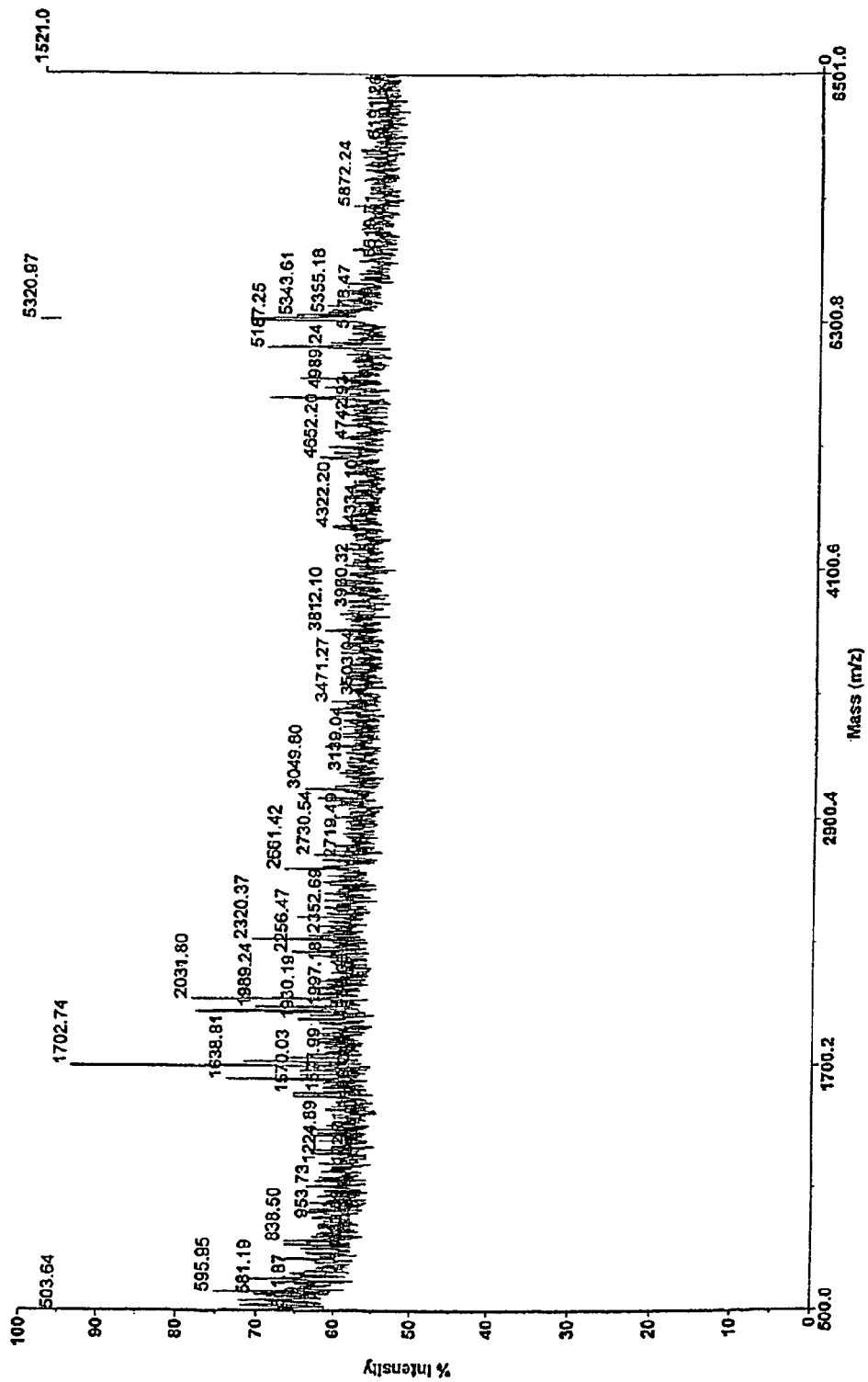

Mass determination of MB2 was accomplished using MALDI-TOF spectrometry analysis on an Applied Biosystems 4115 Voyager system (FIG. 7). Masses were acquired in the 500-8000 Da range in the linear positive ion mode with external calibration. Samples were prepared on a 100 well gold plate by mixing 1 μl of MB2 (100 μM) with a 1 μl matrix solution (9:1 solution of 50 mg/ml 3-hydroxypicolinic acid in 50% acetonitrile and 50 mg/ml ammonium citrate in $H_2O$).

TABLE 1

Gradient elution conditions for HPLC purification of MB2.

| Time (min) | Solvent A (%) $NH_4OAc$ (5% $CH_3CN$) | Solvent B (%) 100% $CH_3CN$ |
|---|---|---|
| 0 | 95 | 5 |
| 10 | 90 | 10 |
| 30 | 80 | 20 |
| 36 | 70 | 30 |
| 45 | 60 | 40 |

Hybridization of MB1 and MB2 with Model Sequences A-14, A14-2dA and dab-14

Model sequences (1.2 μM) were hybridized with 1 μM of MB1 or MB2 in 20 mM triethanolamine buffer, pH 7.6, containing 50, 100 or 200 mM KCl and 5 or 10 mM $MgCl_2$. FIG. 10A-10B show results obtained with MB1 and MB2 and A-14. Samples were heated to 95° C. for 5 min and then cooled slowly to 15° C. over 8-10 hrs. Fluorescence emission spectra of the reaction mixtures were then measured on a SPEX Fluoromax spectrofluorometer using a 3 mm square cuvette. Emission spectra were recorded over the wavelength range 495-580 nm with an excitation wavelength of 490 nm. The spectral bandpass was 5 nm for all emission spectra. Inner filter effects were corrected for the sample concentrations that showed a maximal absorbance at the excitation wavelength of >0.1. The concentrations of oligonucleotides used were typically in the range of 1-2 μM.

The One Pot RTA Assay (FIGS. 9-10)

Reactions were carried out on 2 μM of either A-14 (FIG. 10) or A14-2dA (FIG. 9) in 10 mM potassium citrate buffer (pH 4.0) containing 1 mM EDTA. Substrates were heated to 90° C. for 1 min, cooled on ice, and incubated at 37° C. for 15 min prior to their addition to the assay mix to reduce any variability in the turnover rate that might result from conformational heterogeneity (hairpins v/s other forms) in solution. The total reaction volume was 50 μL. Reactions were started by the addition of RTA at concentrations of 125 nM. After incubation of the reaction vials at 37° C. for 30 min, the reaction pH was adjusted to 7.6 by the addition of 120 μL of 40 mM triethanolamine buffer, pH 8.8. 1.6 μM of MB1 or MB2 were then added followed by 20 μL of 200 mM triethanolamine buffer containing 500 mM KCl and 50 mM $MgCl_2$. The samples were annealed and fluorescence measurements carried out as described earlier.

Thermal Denaturation Experiments

Figure 8A:
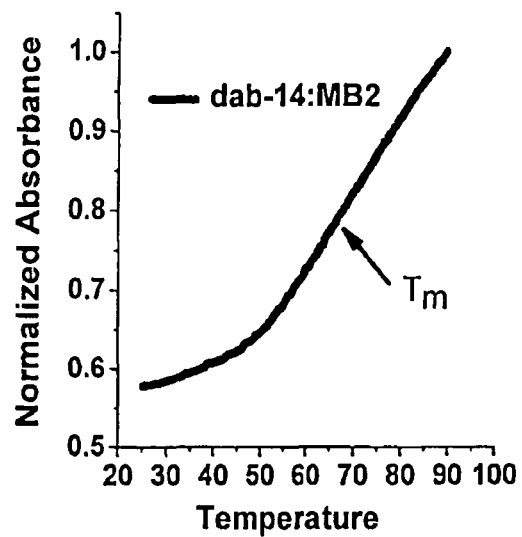
Figure 8B:
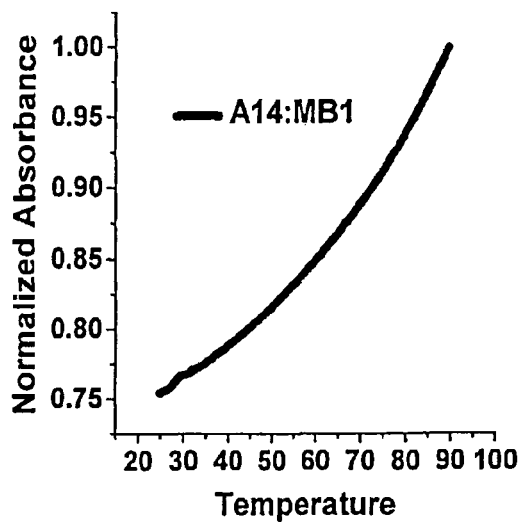

Melting experiments were carried out in 20 mM triethanolamine buffer, pH 7.6, containing 100 mM KCl and 10 mM $MgCl_2$. Sample concentrations were in the range of 1-2 μM for the hairpin beacons and 2-4 μM for the duplexes. Samples were placed in cuvettes of 1 cm pathlength, argon was bubbled through the solutions via a hypodermic syringe needle and 20 μL of silicone oil was placed on the sample to prevent evaporation during the run. The Pelletier system on the Varian Cary 100 spectrophotometer was then employed to heat the samples from 15 or 25° C. to 90 or 95° C. in increments of 0.5° C./min and the absorbance was measured at 260 nm. Melting transitions could not be fit cleanly for any of the samples in this study. It is likely that the high GC content of the samples (~85%) raises the melting temperature of the hairpins and duplexes. Representative melting curve of the dab-14:MB2 and of the A14:MB1 heteroduplexes shown in FIG. 8A-8B illustrate this problem.

Results with A14-2dA in the One Pot Assay

The discrimination efficiency of the pyrene beacon, MB2, for the product of the RTA reaction was found to be better in the one pot system when A14-2dA was used as the substrate instead of A-14. The enhancement of fluorescence of the product relative to A-14 was ~20% whereas an enhancement of ~40% was observed for the product relative to A14-2dA. In the case of A14-2dA, the product of its reaction with RTA generates an abasic deoxyribose site, whereas A-14 generates an abasic ribose site. Since the pyrene sugar is a deoxyribonucleoside, it possibly hybridizes more efficiently with the deoxyribo-abasic site. This might explain the similar discrimination efficiency observed in case of the model sequence, dab-14.

Dependence of Hybridization of Mb2 with A-14 and dab-14 on Salt Concentration

The discrimination between the intact and abasic RNA Sequences in case of the pyrene beacon was found to be dependent on monovalent salt concentration in the hybridization buffer. 50, 100 and 200 mM KCl were used and discrimination was found to decrease with increasing salt concentration. The equilibrium constant and the rate of duplex formation are known to increase at higher cation concentration due to the neutralization of the negative charge of backbone phosphates. Monovalent ions also affect the intercalation of polycyclic aromatic hydrocarbons such as pyrene into duplexes. The effect is more pronounced when these molecules are covalently linked to the oligonucleotides through flexible spacers such as methylene units. Intercalation has also been shown to become stronger for single-stranded oligonucleotides and vice-versa for duplexes as the concentration of the monovalent cation increases (Masuko et al. 1998). Pyrene monomer emission was also followed directly by excitation at 348 nm. However, no discrimination was observed suggesting that despite efficient hybridization with the abasic oligonucleotide, the environment of the pyrene in the both duplexes (that with A-14 and dab-14) might be similar. The intercalation of pyrene into DNA-DNA (Manoharan et al. 1995), DNA-RNA (Yamana et al. 1999) and RNA-RNA (Nakamura et al. 2005) duplexes has been studied. It has been shown that the pyrene-modified RNA duplex completely differs from the pyrene-modified DNA-DNA or DNA-RNA duplex in terms of local structure around the pyrene. The pyrene monomer fluorescence has been found to be considerably quenched in case of DNA duplexes whereas for the RNA-RNA duplex, a red shift observed in pyrene emission has been attributed to its non-intercalated form. Such properties can also be exploited in the future for design of selective probes.

Discrimination between A-14 and dab-14 by MB1

Figure 5:
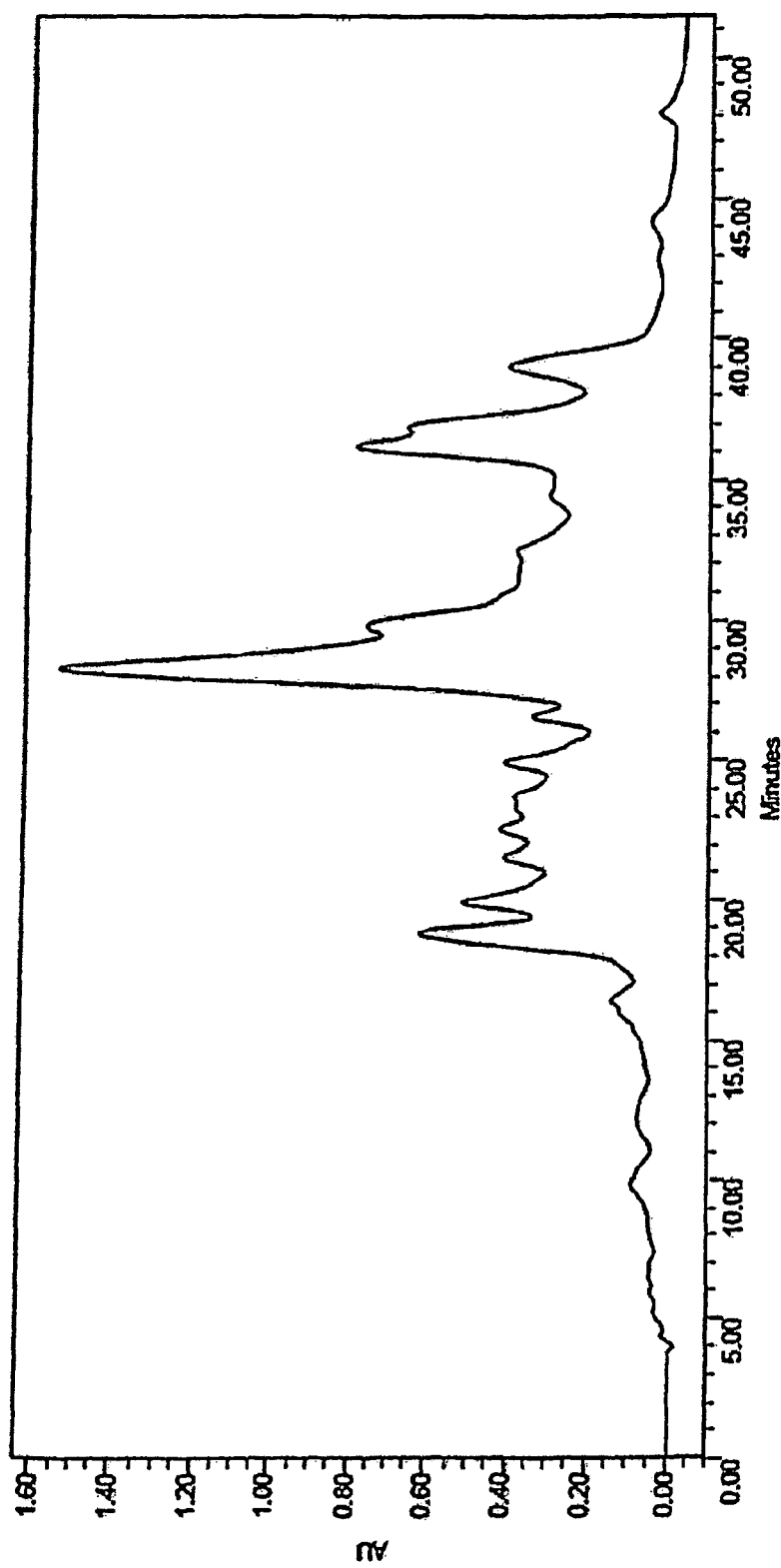
Figure 6:
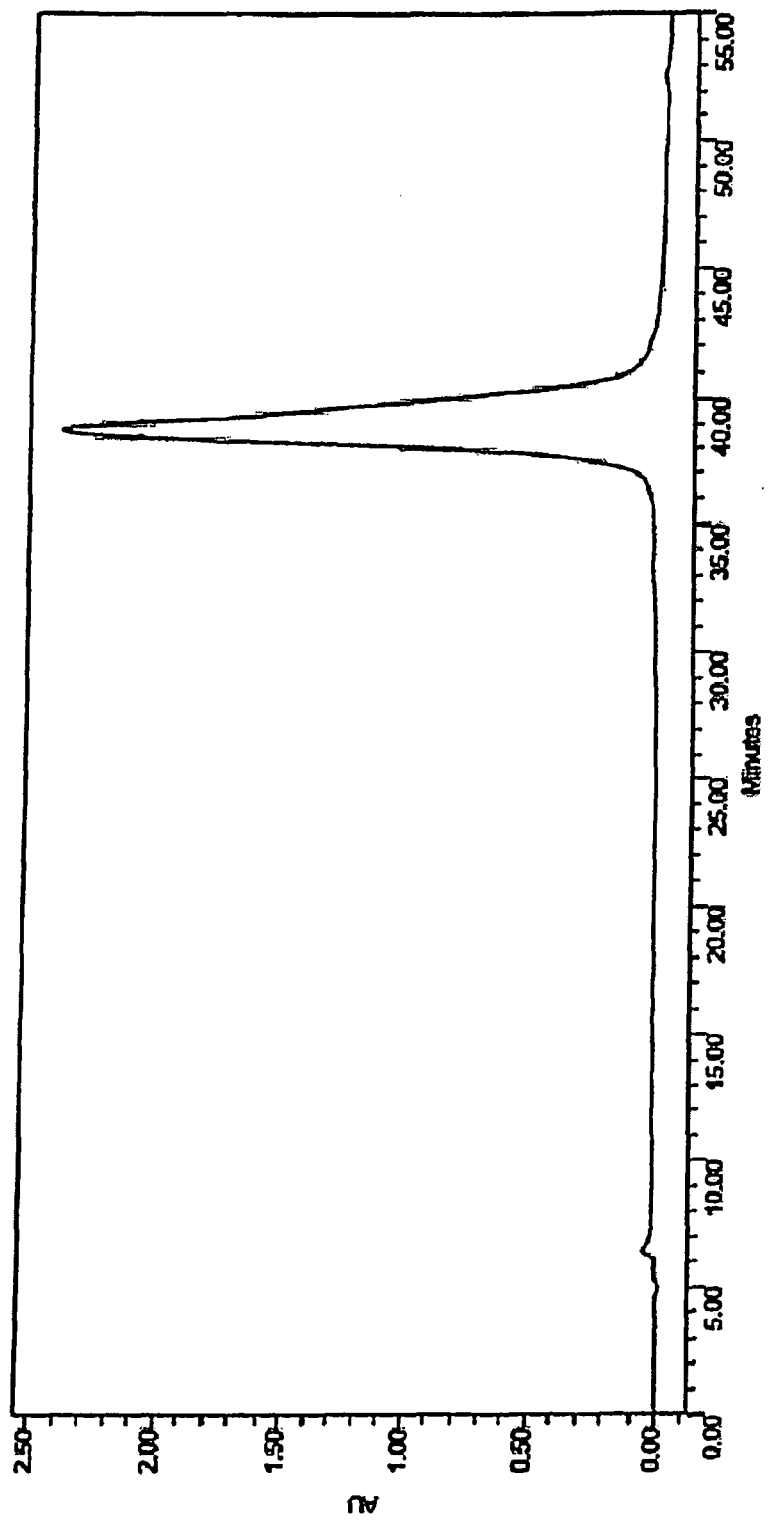

The sequence labeled MB1 in FIGS. 1 and 2A, 5'-6-FAM-d(CGCGCTCTCGCGCG) (SEQ ID NO:1)-BHQ1-3', was designed as the beacon sequence (6-FAM=6-carboxyfluorescein and BHQ1=Black Hole Quencher Dye 1). The program mFold (Zucker 2003) predicts that this structure adopts a tetraloop TCTC hairpin and has a melting temperature ($T_m$) of 79.6° C. There are precedents that demonstrate a dependence of stability of the hairpin loop on closing base pair identity. In particular, a C-G closing base pair provides enhanced stability (Antao et al. 1992). The inventors hypothesized that MB1, would also form a stable hairpin structure and the fluorescence of 5(6)-FAM would be quenched by BHQ-1, in this conformation. MB-1 was chosen in the DNA format mainly for synthetic ease and to ensure good hybridization with a RNA sequence since RNA-DNA heteroduplexes are thermodynamically stable (Lesnik and Freier 1995, Sugimoto et al. 2000). Synthetic sequences, A-14 (5'-CGCGC-GAGAGCGCG-3') (SEQ ID NO:4) and dab-14 (5'-CGCGCGdabGAGCGCG-3') were chosen as models for the RTA substrate and product, respectively. The latter incorporates a deoxyribo-abasic (dab) residue at the second site in the tetraloop to mimic the depurinated product of the RTA reaction. The RTA product has a ribose at this site. Both of these sequences possess the same closing C-G base pair and at room temperature are predicted to exist as hairpins in solution. mFold predicts a $T_m$ of 102.3° C. for A-14 with a hairpin GAGA loop structure as the only conformation.

Complete discrimination between A-14 and dab-14 was achieved upon hybridization of these sequences with MB1 (FIG. 11A) in a 1.2:1 ratio at pH 7.6. The fluorescence of the A14:MB1 duplex was enhanced ~4 fold relative to the fluorescence of the beacon hairpin alone. The fluorescence of the sample with dab-14 remained completely quenched with almost no enhancement over the fluorescence of the parent beacon. Thus, duplex formation was impaired in the case of the sequence with an abasic site. The enhancement in fluorescent intensity ($\lambda_{ex}$=490 nm; $\lambda_{em}$=515 nm) was independent of the salt concentration suggesting that duplex formation between A-14 and MB1 was efficient. Duplex formation overrides the competing formation of individual hairpins indicating that the $T_m$ of the heteroduplex is higher than at least one of the hairpins. The $T_m$ for the MB1:A-14 heteroduplex could not be fitted, although the data suggest that the value exceeds 80° C. indicating high thermodynamic stability.

Discrimination Between A-14 and dab-14 by MB2

Figure 2B:
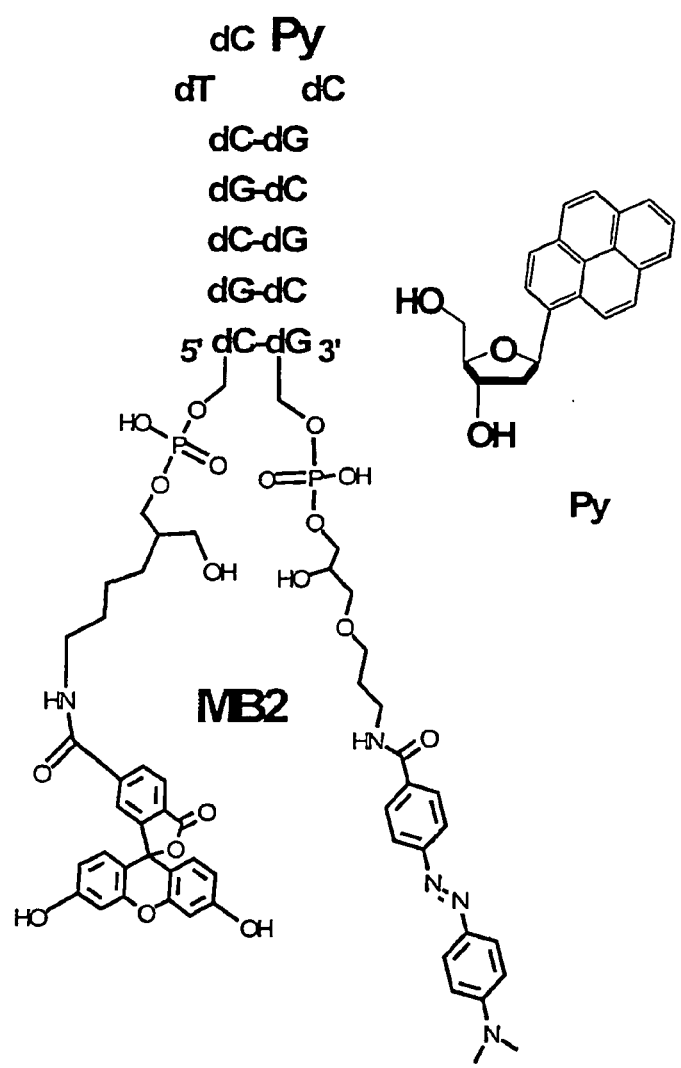

The quenched signal of MB1 in response to an abasic site generated by RTA would yield "negative" monitoring of the reaction since the substrate would brightly fluoresce but not the product. Another beacon, MB2 (FIGS. 1 and 2B; 5'-FAM-d(CGCGCTCPyCGCGCG)-Dab-3') containing a pyrene deoxynucleoside (Py) was designed based on the observations of Matray and Kool (1999) that pyrene can specifically partner abasic sites in duplexes via hydrophobic binding. Thus, the heteroduplex of MB2 with A-14 (a pyrene-adenine pair) would be of similar stability to the heteroduplexes with dab-14 and ab-14. Adapted to the RTA assay, MB2 would result in an enhancement of fluorescence in response to RTA action. The β-anomer of the pyrene 2'-deoxyribonucleoside phosphoramidite was synthesized according to the method of Jiang et al. (2002) and incorporated into the sequence MB2 with dabcyl and fluorescein modifications at the 3' and 5' ends.

Figures 11A, 11B:
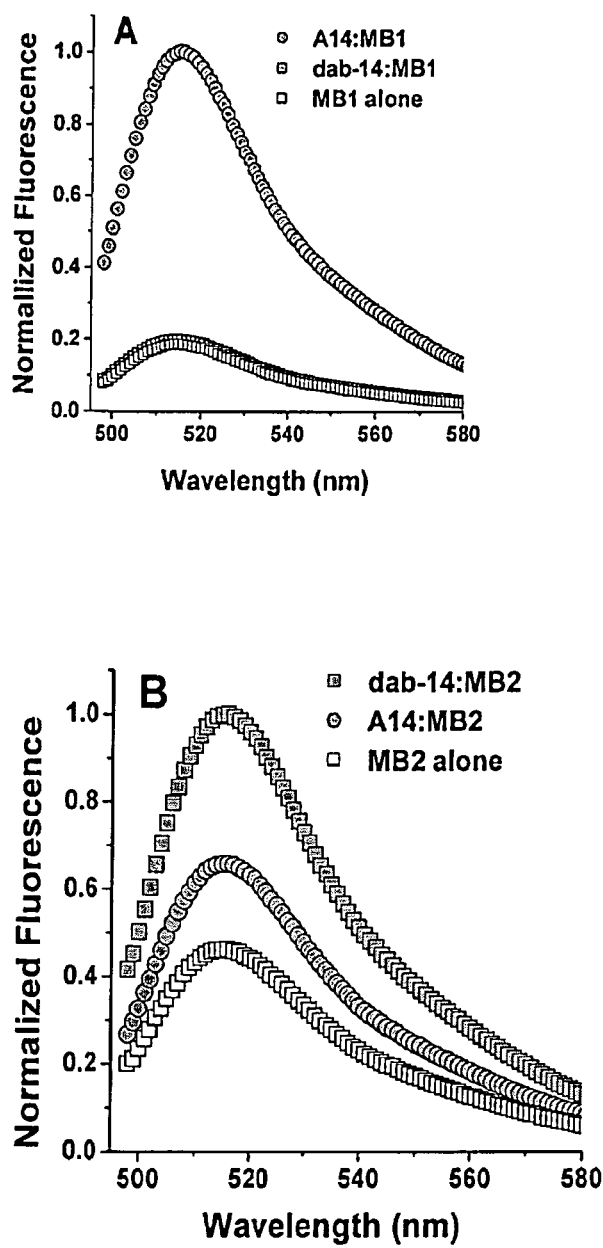
Figure 11C:
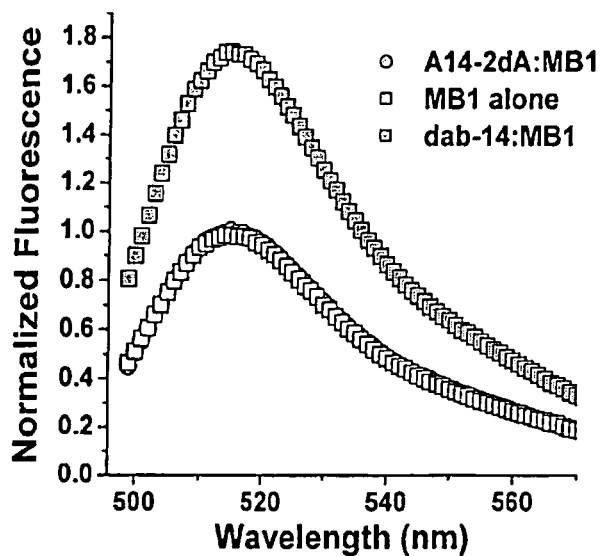

Annealing experiments with the new beacon showed the fluorescence of the A-14:MB2 heteroduplex to be enhanced ~2 fold relative to that of the beacon hairpin alone (FIG. 11B). The dab-14:MB2 duplex fluoresced ~4 fold better. Duplex formation occurs in both cases. As hypothesized, the pyrene beacon hybridized much more efficiently with the abasic RNA than MB1. The discrimination factor between A-14 and dab-14 is lower with the MB2 beacon than with MB1. Nevertheless, the generation of an abasic site in a 14-mer RNA sequence can be conclusively shown using a combination of both beacons. The discrimination with the pyrene beacon was found to be dependent on monovalent salt concentration during hybridization. Intercalation of pyrene into duplexes has been shown to become stronger for single-stranded oligonucleotides and vice-versa for duplexes as the concentration of the monovalent cation increases (Masuko et al. 1998). This might explain the weaker discrimination observed with the pyrene beacon at higher salt concentrations. The $T_m$ for dab- 14:MB2 duplex was determined to be 69° C. Melting transitions of MB2 and other duplexes could not be fit. Hybridization was also studied using A14-2dA (5'-CGCGCGdAGAGCGCG-3') (SEQ ID NO:4), a ~1200 min$^{-1}$ substrate of RTA. Both beacons gave similar results to A-14.

Detection of RTA

Figure 11D:
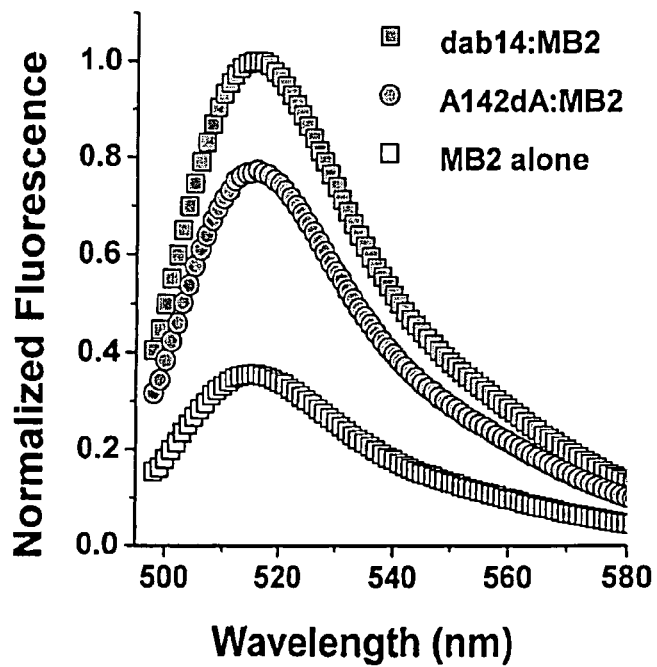

An important consideration in designing a one pot assay for RTA is that its catalytic activity on small stem-tetraloop substrates is optimum at pH 4.0. This pH is incompatible with the fluorophore since the ionization equilibria of fluorescein governing its fluorescent intensity are only favorable above neutral pH. Thus, A-14 was incubated with RTA for 30 min under the ricin assay conditions (Chen et al. 1998), the reaction mixture neutralized with triethanolamine to pH 7.6 and hybridized with either MB1 or MB2. The concentration of RTA chosen in this system ensured complete conversion of substrate to product. The discrimination efficiency of the short beacons was found to be reduced in this one pot system. In the case of MB1 the enhancement of fluorescence for A-14 relative to ab-14 was 20% (discrimination factor of 1.22), whereas in the model system this enhancement was ~40% (discrimination factor of 1.4). Similarly, in the case of the pyrene beacon, MB2, the enhancement of fluorescence of ab-14 relative to A-14 was ~20% whereas in the model system it was ~40%. Discrimination of the product was better with MB2 (~1.4) when A14-2dA was used as the substrate (FIG. 11D). It is likely that the pyrene beacon hybridizes more efficiently with the deoxyribo-abasic site in this case than with the ribo-abasic site in ab-14. The efficiency of hybridization is possibly reduced in this one pot assay format since the pH neutralization step changes the ionic strength of the hybridization buffer. Nevertheless, the trends were similar as with the model sequences.

Additional Substrates and Beacons for Ricin Detection

Additional substrates for RTA that resemble the natural Sarcin-Ricin loop (SRL) of ribosomal RNA can also be used. Examples of the structures of additional substrates and of an additional beacon are shown in FIG. 12. The beacon has a TCTC hairpin loop that will essentially function like MB1. The pyrene nucleoside can similarly be incorporated into the hairpin loop in an analogous fashion to MB2.

Immobilization of Molecular Beacons

The Molecular Beacons can be immobilized on to glass slides to facilitate detection of ricin. Click chemistry can be used to attach the beacons. An immobilization scheme is shown in FIG. 13.

Summary

The present invention discloses DNA beacons that unambiguously distinguish their intact target versus hydrolyzed abasic RNA sequences and can be used to detect the presence of RTA activity. A schematic of an example of the invention is shown in FIG. 14. Fluorescence resonance energy transfer (FRET) between a fluorophore/quencher pair in the 14-mer stem-tetraloop DNA beacons is disrupted only when they are hybridized with RNA sequences that provide a perfect match. One beacon (MB1) hybridizes selectively with the RTA substrate. A second beacon (MB2) incorporates a pyrene deoxynucleoside for specific recognition of the abasic site and hybridizes efficiently with the product of the RTA reaction.

REFERENCES

Antao, V. P.; Tinoco, I. Jr. Thermodynamic parameters for loop formation in RNA and DNA hairpin tetraloops. Nucleic Acids Res. 1992, 20: 819-24.

Baluna R. et al. Evidence for a structural motif in toxins and interleukin-2 that may be responsible for binding to endothelial cells and initiating vascular leak syndrome. Proc Natl Acad Sci USA. 1999, 96(7):3957-62.

Chen, X. Y.; Link, T. M.; Schramm, V. L. Ricin A-chain: kinetics, mechanism, and RNA stem-loop inhibitors. Biochemistry 1998, 37:11605-11613.

Eiklid, K.; Olsnes, S.; Pihl, A. Entry of lethal doses of abrin, ricin and modeccin into the cytosol of HeLa cells. Exp. Cell Res. 1980, 126: 321-326.

Endo, Y.; Chan, Y. L.; Lin, A.; Tsurugi, K.; Wool, I. G. The cytotoxins alpha-sarcin and ricin retain their specificity when tested on a synthetic oligoribonucleotide (35-mer) that mimics a region of 28 S ribosomal ribonucleic acid. J. Biol. Chem. 1988, 263: 7917-7920.

Engert, A et al. The emerging role of ricin A-chain immunotoxins in leukemia and lymphoma. Curr Top Microbiol Immunol. 1998, 234:13-33.

Fredriksson, S. A.; Hulst, A. G.; Artursson, E.; de Jong, A. L.; Nilsson, C.; van Baar, B. L. Forensic identification of neat ricin and of ricin from crude castor bean extracts by mass spectrometry. Anal Chem. 2005 Mar. 15; 77(6):1545-55.

Hesselberth, J R et al. In vitro selection of RNA molecules that inhibit the activity of ricin A-chain. J Biol Chem. 2000, 275(7):4937-42.

Jiang, Y. L.; Stivers, J. T.; Song, F. Base-flipping mutations of uracil DNA glycosylase: substrate rescue using a pyrene nucleotide wedge. Biochemistry. 2002, 41(37):11248-54.

Kirby, R.; Cho, E. J.; Gehrke, B.; Bayer, T.; Park, Y. S.; Neikirk, D. P.; McDevitt, J. T.; Ellington, A. D. Aptamer-based sensor arrays for the detection and quantitation of proteins. Anal Chem. 2004, 76(14):4066-75.

Lesnik, E. A.; Freier, S. M. Relative thermodynamic stability of DNA, RNA, and DNA:RNA hybrid duplexes: relationship with base composition and structure. Biochemistry. 1995, 34(34):10807-15.

Maliuchenko, N. V.; Agapov, Tonevitskii, A. G.; Moisenovich, M. M.; Savvateev, M. N.; Tonevitskii, E. A.; Bykov, V. A.; Kirpichnikov, M. P. [Detection of immune complexes using atomic force microscopy] Biofizika. 2004, 49(6): 1008-14. In Russian.

Manoharan, M.; Tivel, K. L.; Zhao, M.; Nafisi, K.; Netzel, T. L. J. Phys. Chem. 1995, 99: 17461-17472.

Masuko, M.; Ohtani, H.; Ebata, K.; Shimadzu, A. Optimization of excimer-forming two-probe nucleic acid hybridization method with pyrene as a fluorophore. Nucleic Acids Res. 1998, 26(23):5409-16.

Matray, T. J.; Kool, E. T. A specific partner for abasic damage in DNA. Nature. 1999, 399(6737):704-8.

Nakamura, M.; Fukunaga, Y.; Sasa, K.; Ohtoshi, Y.; Kanaori, K.; Hayashi, H.; Nakano, H.; Yamana, K. Pyrene is highly emissive when attached to the RNA duplex but not to the DNA duplex: the structural basis of this difference. Nucleic Acids Res. 2005 Oct. 19; 33(18):5887-95.

O'Toole, J E et al. Clinical trials with blocked ricin immunotoxins. Curr Top Microbiol Immunol. 1998, 234:35-56.

Remnick, D. Washington Post, 1992, Apr. 21, DI.

Ren, R. X.-F.; Chaudhuri, N. C.; Paris, P. L.; Rumney I V, S.; Kool, E. T. J. Am. Chem. Soc. 1996, 118: 7671-7678.

Rubina, A. Y.; Dyukova, V. I.; Dementieva, E. I.; Stomakhin, A. A.; Nesmeyanov, V. A.; Grishin, E. V.; Zasedatelev, A. S. Quantitative immunoassay of biotoxins on hydrogel-based protein microchips. Anal Biochem. 2005 May 15; 340(2): 317-29.

Seo T. S., Bai X., Kim D. H., Meng Q., Shi S., Ruparel H., Li Z., Turro N. J., Ju J. Four-color DNA sequencing by synthesis on a chip using photocleavable fluorescent nucleotides. *PNAS*, 2005, 102: 5926-5931.

Shyu, H. F.; Chiao, D. J.; Liu, H. W.; Tang, S. S. Monoclonal antibody-based enzyme immunoassay for detection of ricin. Hybrid Hybridomics. 2002, 21(1):69-73.

Sugimoto, N.; Nakano, M.; Nakano, S. Thermodynamics-structure relationship of single mismatches in RNA/DNA duplexes. Biochemistry. 2000, 39(37):11270-81.

Yamana, K.; Iwase, R.; Furutani, S.; Tsuchida, H.; Zako, H.; Yamaoka, T.; Murakami, A. 2'-Pyrene modified oligonucleotide provides a highly sensitive fluorescent probe of RNA. Nucleic Acids Res. 1999, 27(11):2387-92.

Yan, X et al. Structure-based identification of a ricin inhibitor. J Mol Biol. 1997, 266(5):1043-9.

Zuker, M. Mfold web server for nucleic acid folding and hybridization prediction. Nucleic Acids Res. 2003, 31(13): 3406-15.

What is claimed is:

1. A fluorescent probe for detecting the presence or absence of an enzyme that catalyzes the release of adenine from a GAGA RNA tetraloop, the fluorescent probe comprising:
   a fluorophore,
   a quencher,
   and a nucleic acid that forms a hairpin loop,
   wherein the hairpin loop comprises TCXC,
   where C is cytidylate or deoxycytidylate, T is thymidylate, and X is T or a pyrene deoxynucleoside.

2. The fluorescent probe of claim 1, wherein the nucleic acid is 9-21 nucleotides in length.

3. The fluorescent probe of claim 1, wherein the nucleic acid is DNA.

4. The fluorescent probe of claim 1, wherein the nucleic acid is RNA.

5. The fluorescent probe of claim 1, wherein the nucleic acid is DNA and RNA.

6. The fluorescent probe of claim 1, wherein the fluorophore is a fluorescein, a rhodamine, a cyanine, or TAMRA.

7. The fluorescent probe of claim 6, wherein the fluorescein is 6-carboxyfluorescein.

8. The fluorescent probe of claim 1, wherein the quencher is Black Hole Quencher Dye 1, Black Hole Quencher Dye 2, or a dabcyl group.

9. The fluorescent probe of claim 1, wherein the fluorescent probe has the formula:

$$5'-F-(X_A)_{2-7}X_B TCXCX'_B(X'_A)_{2-7}-Q-3',$$

wherein $X_A$ and $X'_A$ are nucleotides selected from A (adenylate or deoxyadenylate), C (cytidylate or deoxycytidylate), G (guanylate or deoxyguanylate), T (thymidylate) and U (uridylate); wherein $(X_A)_{2-7}$ and $(X'_A)_{2-7}$ are 2 to 7 nucleotides in length; wherein $(X_A)_{2-7}$ is the same number of nucleotides as $(X'_A)_{2-7}$; and wherein each nucleotide in $(X_A)_{2-7}$ is a complementary base pair with the nucleotide in the corresponding location in $(X'_A)_{2-7}$; wherein one of $X_B$ and $X'_B$ is C and the other is G;

wherein F is a fluorescein, a rhodamine, a cyanine, or TAMRA;

wherein Q is Black Hole Quencher Dye 1, Black Hole Quencher Dye 2, or a dabcyl group; and wherein X is T or a pyrene deoxynucleoside.

10. The fluorescent probe of claim 9, wherein the probe has the formula:

$$5'-F-CGCGCTCXCGCGCG-Q-3',$$

wherein C is deoxycytidylate and G is deoxyguanylate.

11. The fluorescent probe of claim 10, wherein the probe has the formula:

$$5'-F-(CGCGCTCTCGCGCG)(SEQ\ ID\ NO:\ 1)-Q-3'.$$

12. The fluorescent probe of claim 10, wherein the probe has the formula:

$$5'-F-CGCGCTCPyCGCGCG-Q-3',$$

wherein Py is a pyrene deoxynucleoside.

13. The fluorescent probe of claim 9, wherein the probe has the formula:

$$5'-F-CGCTCXCGCG-Q-3',$$

wherein C is deoxycytidylate and G is deoxyguanylate.

14. The fluorescent probe of claim 13, wherein the probe has the formula:

$$5'-F-(CGCTCTCGCG)(SEQ\ ID\ NO:\ 2)-Q-3'.$$

15. The fluorescent probe of claim 13, wherein the probe has the formula:

$$5'-F-CGCTCPyCGCG-Q-3',$$

wherein Py is a pyrene deoxynucleoside.

16. The fluorescent probe of claim 1, wherein the probe has the structure:

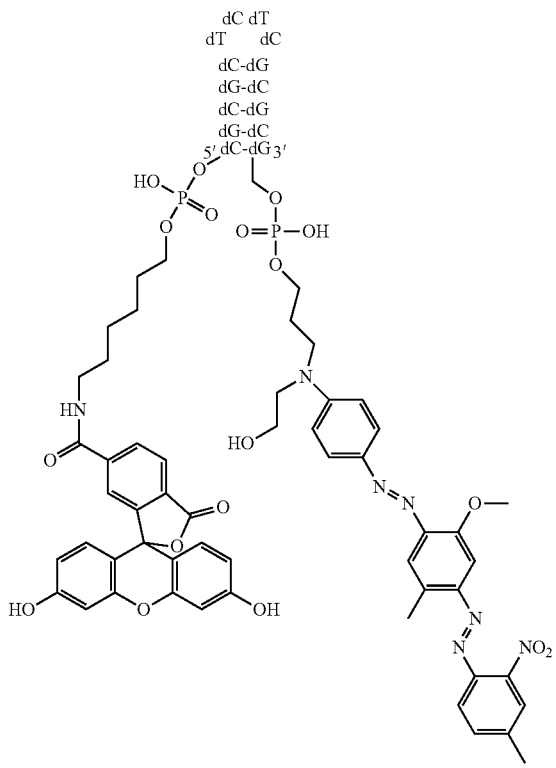

wherein dC is deoxycytidylate, dG is deoxyguanylate, and dT is thymidylate.

17. The fluorescent probe of claim 1, wherein the probe has the structure:

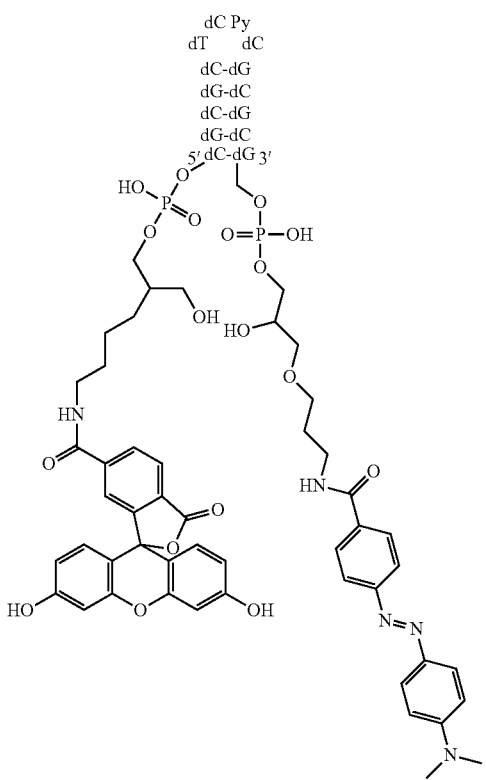

where Py is

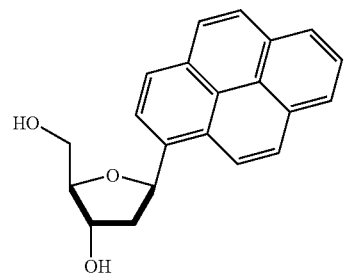

and
wherein dC is deoxycytidylate, dG is deoxyguanylate, and dT is thymidylate.

18. The fluorescent probe of claim 1, wherein the fluorescent probe has the formula:

$$5'-F-(X_A)_{1-6}GX_AX_BTCXCX'_BX'_A(X'_A)_{1-6}-Q-3',$$

wherein G is guanylate or deoxyguanylate;
wherein $X_A$ and $X'_A$ are nucleotides selected from A (adenylate or deoxyadenylate), C (cytidylate or deoxycytidylate), G (guanylate or deoxyguanylate), T (thymidylate) and U (uridylate); wherein $(X_A)_{1-6}$ and $(X'_A)_{1-6}$ are 1 to 6 nucleotides in length; wherein $(X_A)_{1-6}$ is the same number of nucleotides as $(X'_A)_{1-6}$; and wherein each nucleotide in $(X_A)_{1-6}$ is a complementary base pair with the nucleotide in the corresponding location in $(X'_A)_{1-6}$;
wherein one of $X_B$ and $X'_B$ is C and the other is G;
wherein F is a fluorescein, a rhodamine, a cyanine, or TAMRA;
wherein Q is Black Hole Quencher Dye 1, Black Hole Quencher Dye 2, or a dabcyl group; and
wherein X is T or a pyrene deoxynucleoside.

19. The fluorescent probe of claim 18, wherein the probe has the formula:

$$5'-F-X_AX_AX_AX_AGX_AX_BTCXCX'_BX'_AX'_AX'_AX'_AX'_A-Q-3'.$$

20. The fluorescent probe of claim 19, wherein the probe has the formula:

$$5'-F-CGCUGACTCXCGGAGCG-Q-3'.$$

21. The fluorescent probe of claim 20, wherein the probe has the formula:

$$5'-F-CGCUGACTCTCGGAGCG(SEQ\ ID\ NO:\ 3)-Q-3'.$$

22. The fluorescent probe of claim 20, wherein the probe has the formula:

$$5'-F-CGCUGACTCPyCGGAGCG-Q-3',$$

wherein Py is a pyrene deoxynucleoside.

23. The fluorescent probe of claim 1, wherein the fluorescent probe binds to a substrate for the enzyme.

24. The fluorescent probe of claim 1, wherein the fluorescent probe binds to a reaction product created by catalysis of a substrate by the enzyme.

25. The fluorescent probe of claim 1, wherein the presence of the enzyme is indicated by an increase in fluorescent intensity.

26. The fluorescent probe of claim 1, wherein the presence of the enzyme is indicated by a decrease in fluorescent intensity.

27. The fluorescent probe of claim 1, wherein the enzyme is ricin.

28. The fluorescent probe of claim 1, wherein the enzyme is saporin, trichosanthin, gelonin or cinnamonin.

29. A kit for detecting the presence or absence of an enzyme that catalyzes the release of adenine from a GAGA RNA tetraloop, wherein the kit comprises one or more fluorescent probes of claim 1.

30. A method of detecting the presence or absence of an enzyme that catalyzes the release of adenine from a GAGA RNA tetraloop, the method comprising contacting a fluorescent probe with a substrate for the enzyme or with a reaction product created by catalysis of the substrate by the enzyme, under conditions appropriate for the enzyme to catalyze the substrate, wherein a change in intensity of the fluorescent probe indicates that the substrate has been cleaved by the enzyme and that the enzyme is present and an absence of change in intensity in the fluorescent probe indicates the absence of the enzyme, wherein the fluorescent probe is a fluorescent probe of claim 1.

\* \* \* \* \*

```
                             SEQUENCE LISTING

<160> NUMBER OF SEQ ID NOS: 6

<210> SEQ ID NO 1
<211> LENGTH: 14
<212> TYPE: DNA
<213> ORGANISM: Artificial Sequence
<220> FEATURE:
<223> OTHER INFORMATION: nucleotide sequence for fluorescent probe

<400> SEQUENCE: 1
cgcgctctcg cgcg                                                         14

<210> SEQ ID NO 2
<211> LENGTH: 10
<212> TYPE: DNA
<213> ORGANISM: Artificial Sequence
<220> FEATURE:
<223> OTHER INFORMATION: nucleotide sequence for fluorescent probe

<400> SEQUENCE: 2
cgctctcgcg                                                              10

<210> SEQ ID NO 3
<211> LENGTH: 17
<212> TYPE: DNA
<213> ORGANISM: Artificial Sequence
<220> FEATURE:
<223> OTHER INFORMATION: nucleotide sequence for fluorescent probe

<400> SEQUENCE: 3
cgcugactct cggagcg                                                      17

<210> SEQ ID NO 4
<211> LENGTH: 14
<212> TYPE: DNA
<213> ORGANISM: Artificial Sequence
<220> FEATURE:
<223> OTHER INFORMATION: nucleotide sequence for substrate for detecting
      presence or absence of enzyme that catalyzes the release of
      adenine from a GAGA RNA tetraloop
<220> FEATURE:
<221> NAME/KEY: misc_feature
<222> LOCATION: (7)..(7)
<223> OTHER INFORMATION: A at position 7 is adenylate or deoxyadenylate

<400> SEQUENCE: 4
cgcgcgagag cgcg                                                         14

<210> SEQ ID NO 5
<211> LENGTH: 17
<212> TYPE: DNA
<213> ORGANISM: Artificial Sequence
<220> FEATURE:
```

```
<223> OTHER INFORMATION: nucleotide sequence for substrate for detecting
      presence or absence of enzyme that catalyzes the release of
      adenine from a GAGA RNA tetraloop
<220> FEATURE:
<221> NAME/KEY: misc_feature
<222> LOCATION: (9)..(9)
<223> OTHER INFORMATION: A at position 9 is adenylate or deoxyadenylate

<400> SEQUENCE: 5
cgcugacgag aggagcg                                                17

<210> SEQ ID NO 6
<211> LENGTH: 10
<212> TYPE: DNA
<213> ORGANISM: Artificial Sequence
<220> FEATURE:
<223> OTHER INFORMATION: nucleotide sequence for substrate for detecting
      presence or absence of enzyme that catalyzes the release of
      adenine from a GAGA RNA tetraloop
<220> FEATURE:
<221> NAME/KEY: misc_feature
<222> LOCATION: (5)..(5)
<223> OTHER INFORMATION: A at position 5 is adenylate or deoxyadenylate

<400> SEQUENCE: 6
cgcgagagcg                                                        10
```